US009984279B2

(12) United States Patent
Fisher et al.

(10) Patent No.: US 9,984,279 B2
(45) Date of Patent: *May 29, 2018

(54) APPARATUS, SYSTEM, AND METHOD FOR IMAGE NORMALIZATION USING A GAUSSIAN RESIDUAL OF FIT SELECTION CRITERIA

(71) Applicant: Luminex Corporation, Austin, TX (US)

(72) Inventors: Matthew S. Fisher, Austin, TX (US); Nicolas Arab, Austin, TX (US)

(73) Assignee: Luminex Corporation, Austin, TX (US)

( * ) Notice: Subject to any disclaimer, the term of this patent is extended or adjusted under 35 U.S.C. 154(b) by 184 days.

This patent is subject to a terminal disclaimer.

(21) Appl. No.: 15/004,485

(22) Filed: Jan. 22, 2016

(65) Prior Publication Data

US 2016/0232396 A1 Aug. 11, 2016

Related U.S. Application Data

(63) Continuation of application No. 13/918,540, filed on Jun. 14, 2013, now Pat. No. 9,245,169.

(60) Provisional application No. 61/660,270, filed on Jun. 15, 2012.

(51) Int. Cl.
*G06K 9/00* (2006.01)
*G01N 15/10* (2006.01)
*G01N 15/14* (2006.01)

(52) U.S. Cl.
CPC ....... *G06K 9/0014* (2013.01); *G01N 15/1012* (2013.01); *G01N 15/1434* (2013.01); *G01N 15/1456* (2013.01); *G01N 15/1463* (2013.01); *G06K 9/00134* (2013.01); *G06K 9/00147* (2013.01); *G01N 2015/1006* (2013.01)

(58) Field of Classification Search
None
See application file for complete search history.

(56) References Cited

U.S. PATENT DOCUMENTS 3,824,393 A 7/1974 Brain
6,927,401 B1 8/2005 Palo
(Continued)

FOREIGN PATENT DOCUMENTS

CN 1524925 9/2004
CN 1774200 5/2006
(Continued)

OTHER PUBLICATIONS

Extended European Search Report in Application No. 13804717.0 dated Feb. 8, 2016, 6 pages.
(Continued)

*Primary Examiner* — Nirav G Patel
(74) *Attorney, Agent, or Firm* — Meyertons, Hood, Kivlin, Kowert & Goetzel, P.C.

(57) ABSTRACT

An apparatus and method for image normalization using a Gaussian residual of fit selection criteria. The method may include acquiring a two-dimensional image of a plurality of particles, where the plurality of particles comprises a plurality of calibration particles, and identifying a calibration particle by correlating a portion of the image corresponding to the calibration particle to a mathematical model (e.g. Gaussian fit). The measured intensity of the calibration particle may then be used to normalize the intensity of the image.

20 Claims, 3 Drawing Sheets

100
Start
102 Acquire a 2-D image of a plurality of particles
104 Identify a calibration particle by correlating the image of a calibration particle to a mathematical formula
106 Measure an intensity of the calibration particle
108 Use the intensity of the calibration particle to normalize the 2-D image
End

(56) References Cited

U.S. PATENT DOCUMENTS

| | | | |
|---|---|---|---|
| 2004/0042646 | A1 | 3/2004 | MacAulay et al. |
| 2006/0238757 | A1 | 10/2006 | Silcott |
| 2010/0285594 | A1 | 11/2010 | Purvis, Jr. |
| 2012/0002040 | A1 | 1/2012 | Roth et al. |
| 2012/0002194 | A1 | 1/2012 | Roth et al. |
| 2012/0002882 | A1 | 1/2012 | Roth |

FOREIGN PATENT DOCUMENTS

| | | |
|---|---|---|
| EP | 1175602 | 1/2002 |
| JP | 2009-509270 | 3/2009 |

OTHER PUBLICATIONS

International Search Report and Written Opinion in Application No. PCT/US2013/046035 dated Nov. 29, 2013, 8 pages.

International Preliminary Report in Application No. PCT/US2013/046035 dated Dec. 16, 2014, 5 pages.

Jonas Ries, "Advanced Fluorescence Correlation Techniques to Study Membrane Dynamics," Technische Universitat Dresden, 2008, 165 pages.

Office Action in U.S. Appl. No. 13/918,540 dated Apr. 28, 2015, 8 pages.

Office Action in Chinese Application No. 201380031436.0 dated Aug. 2, 2016, 23 pages.

Office Action in Japanese Application No. 2015-517472 dated Oct. 25, 2016, 5 pages.

Office Action in Chinese Application No. 201380031436.0 dated Apr. 1, 2017, 5 pages.

APPARATUS, SYSTEM, AND METHOD FOR IMAGE NORMALIZATION USING A GAUSSIAN RESIDUAL OF FIT SELECTION CRITERIA

CROSS REFERENCE TO RELATED APPLICATIONS

The present application is a continuation of U.S. application Ser. No. 13/918,540, filed Jun. 14, 2013 (now U.S. Pat. No. 9,245,169), which claims priority to U.S. Provisional Appl. No. 61/660,270, filed on Jun. 15, 2012; the disclosures of each of the above-referenced applications are incorporated by reference herein in their entireties.

BACKGROUND OF THE INVENTION

Field of the Invention

This invention relates to methods and systems for image data processing and more particularly relates to an apparatus system and method for image normalization using a Gaussian residual of fit selection criteria.

Description of the Related Art

Imaging using detectors such as charged coupled device (CCD) detectors is employed in several currently-available instruments in biotechnology applications. Many of the commercially available systems are configured to image target human (or other animal) cells. For multiplexed applications in which CCD detectors are used to measure fluorescent emission of cells, the position of the cells and the fluorescent emission within the image may be used to characterize the cells.

SUMMARY OF THE INVENTION

An method for normalizing an image is presented. In one embodiment, the method includes acquiring a two-dimensional image of a plurality of particles, where the plurality of particles comprises a plurality of calibration particles. In addition, the method may include the step of identifying a calibration particle by correlating a portion of the image corresponding to the calibration particle to a mathematical model. Furthermore, the method may include measuring an intensity of the calibration particle and utilizing the intensity of the calibration particle to normalize the intensity of the image.

In some embodiments, the calibration particle is internally dyed. In some embodiments, the method may also include identifying a plurality of calibration particles, where the plurality of calibration particles are distributed into a plurality of regions of the two-dimensional image. In addition, the method may include utilizing an intensity of the plurality of calibration particles to normalize an intensity of the plurality of regions.

In some embodiments, the method may include utilizing the intensity of the calibration particle to normalize the intensity of a second two-dimensional image of the plurality of particles. For example, the second two-dimensional image may be a classification image.

In some embodiments, the mathematical model may be a Gaussian mathematical model. In some embodiments, the mathematical model may be a quadratic mathematical model.

In some embodiments, measuring the intensity of the calibration particle may include detecting a peak of the calibration particle. In addition, measuring the intensity of the calibration particle may include integrating an area of the image around a center of the calibration particle.

In some embodiments, the method may include subtracting a background signal from the two-dimensional image before identifying the calibration particle.

Tangible computer-readable media are also presented. The tangible computer-readable media may include instructions, that when executed by a computer, cause the computer to perform the methods described herein.

The term "coupled" is defined as connected, although not necessarily directly, and not necessarily mechanically.

The terms "a" and "an" are defined as one or more unless this disclosure explicitly requires otherwise.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
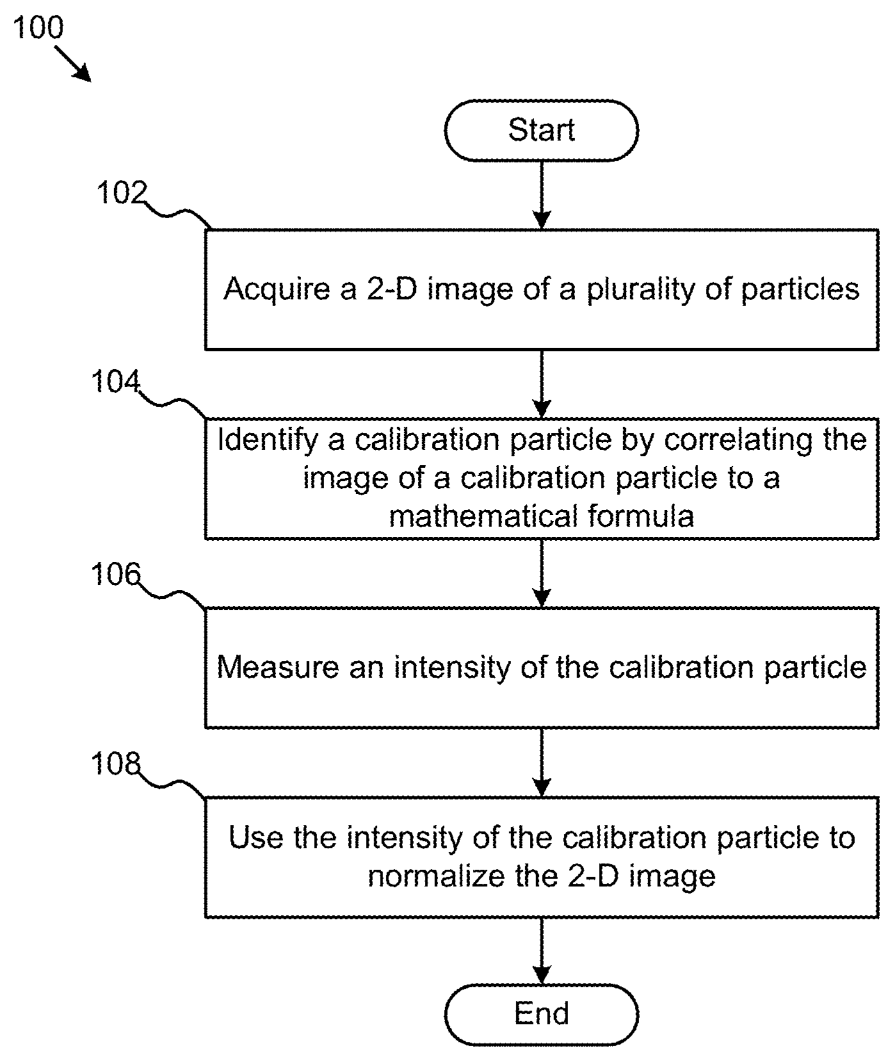
FIG. 1 is a flow chart illustrating one embodiment of a method for normalizing an image.

Various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, or non-organic matter, for example. The particles may serve as vehicles for molecular reactions. Examples of appropriate particles are illustrated and described in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. Without limitation, the systems and methods described herein may be used with any of the particles described in these patents. In addition, particles for use in method and system embodiments described herein may be obtained from manufacturers such as Luminex Corporation of Austin, Tex.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated and described in U.S. Pat. No. 6,268,222 to Chandler et al. and U.S. Pat. No. 6,649,414 to Chandler et al., which are incorporated by reference as if fully set forth herein. The types of particles that can be used in the methods and systems described herein also include particles having one or more fluorochromes or fluorescent dyes incorporated into the core of the particles. For example, calibration particles may be internally and uniformly dyed. In some embodiments a calibration particle may be internally dyed with a plurality of dyes.

Particles that can be used in the methods and systems described herein further include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles. As described below, image data processing may include classification of the particles, particularly for a multi-analyte fluid, as well as a determination of the amount of analyte bound to the particles. Since a reporter signal, which represents the amount of analyte bound to the particle, is typically unknown during operations, specially dyed particles, which not only emit fluorescence in the classification wavelength(s) or wavelength band(s) but also in the reporter wavelength or wavelength band, may be used for the processes described herein.

The methods described herein generally include analyzing one or more images of particles and processing data measured from the images to determine one or more characteristics of the particles. For example, the processing of data may be used to determine normalized numerical values representing the magnitude of fluorescence emission of the particles at multiple detection wavelengths in multiple regions of an image. Subsequent processing of the one or more characteristics of the particles, such as using one or more of the numerical values to determine a token ID representing the multiplex subset to which the particles belong and/or a reporter value representing a presence and/or a quantity of analyte bound to the surface of the particles, can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, and U.S. Pat. No. 6,939,720 to Chandler et al., which are incorporated by reference as if fully set forth herein.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

FIG. 1 illustrates one embodiment of a method 100 for image normalization using a mathematical model (e.g. Gaussian) residual of fit selection criteria. In one embodiment, the method 100 begins with the step 102 of acquiring a two-dimensional image of a plurality of particles. The image may be taken, for example, with a CCD sensor. In some embodiments, multiple images may be taken. For example, two classification channel images and a reporter image may be taken. The plurality of particles may include a plurality of calibration particles. Calibration particles may be, for example, triple-dyed particles. The dyes may be evenly distributed throughout the calibration particles, which may result in an evenly distributed fluorescence in the reporter channel when the calibration particles are illuminated with an excitation light source. In some embodiments, all particles (calibration particles and assay particles) will have evenly distributed fluorescence in the classification channels. However, only calibration particles will have evenly distributed fluorescence in the reporter channel. Evenly distributed fluorescence may cause a Gaussian distribution of light in an image corresponding to the particle due to the spherical shape of a particle.

Step 104 recites identifying a calibration particle by correlating a portion of the image that corresponds to the calibration particle to a mathematical formula. This step may include some sub-components. For example, the method may first include subtracting out a background signal from the image and then detecting the peaks in the image that correspond to individual particles. Once the location of the particles are known, the method may include performing a numerical fit to the image pixels around the detected peaks. In one embodiment, the numerical fit may be a Gaussian fit of the equation in the form of:

$$g(u,v)=a*e^{-b*(u^2+v^2)}$$

The fit process determines the parameters a and b that best fit the image of the particle. The fit may be done in sub-pixel resolution, such as by interpolating pixels to increase the resolution of the image used to perform the fit. The residual of the fit may be measured and if the residual is above a predetermined value (a tolerance), the particle may be rejected as not being a calibration particle. Calibration particles may have Gaussian profiles due to being internally dyed. By contrast, assay particles, which may have fluorescence solely on the surface of the particle, may not have a Gaussian distribution. As such, calibration particles may be identified by their Gaussian profiles. Although the profiles of calibration particles is described generally as Gaussian, in some embodiments, the mathematical formula to perform the fit may be quadratic, for example. Different formulas may reduce the processing required to determine the fit at the expense of reduced accuracy in detecting calibration particles. In addition, in practice, additional steps, such as discarding outlier particles, may be used to increase the performance of the system.

Method 100 also includes the step 106 of measuring an intensity of the calibration particle. The intensity of the particle may be measured by measuring the peak of the measured signal, or it may be measured by integrating the pixels within a particular radius of the measured peak. Additionally, the intensity may be measured by first determining a sub-pixel image of the particle, such as through interpolation, and then integrating the sub-pixel image around a peak of the particle.

Certain parameters of that calibration particle are known. For example, a calibration particle may have a known size and amount of fluorescent material that are established when the calibration particles are manufactured. For example, the amount of different dyes used to manufacture the calibration particles can be carefully controlled to ensure a known amount and even distribution of fluorescence.

Method 100 also includes the step 108 of using the intensity of the calibration particle to normalize the two-dimensional image. Because the expected amount of fluorescence of the calibration particle is known, that amount of fluorescence may be used to normalize the measured amount of fluorescence intensity. Moreover, this process may be repeated for a plurality of calibration particles distributed throughout the 2-D image to normalize different areas of the image. Because calibration particles can be interspersed with assay particles, the image may be normalized without having to take a separate image with calibration particles alone. Thus, the throughput may be increased while maintaining normalized intensity of multiple images. The lack of uniformity of image intensity may be caused by light source non-uniformity, lens nonuniformity, or movement of the imaging plane, for example. The methods described herein may be able to simultaneously normalize for a plurality of causes of non-uniform light measurements.

The normalization of the image intensity may be used when multiple images are taken of the same set of particles. For example, two separate images may be taken of classification channel and one in a reporter channel. The calibration particles may show up in all three images and may be used to normalize all three images.

Figure 2:
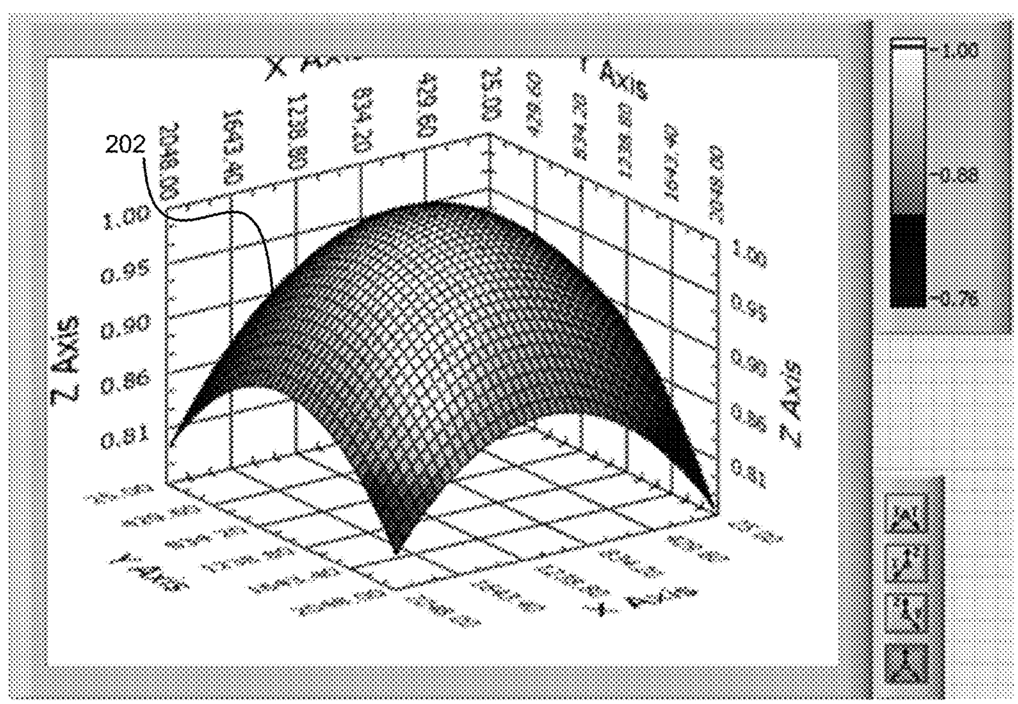
FIG. 2 is a three-dimensional representation of a two-dimensional image of a calibration particle.

FIG. 2 describes a portion of a two-dimensional image where the intensity of measured light 202 from a particle is shown on the z-axis. In this situation, the measured light 202 is Gaussian in form. That information may be used to identify a particle as a calibration particle as described above.

Figure 3:
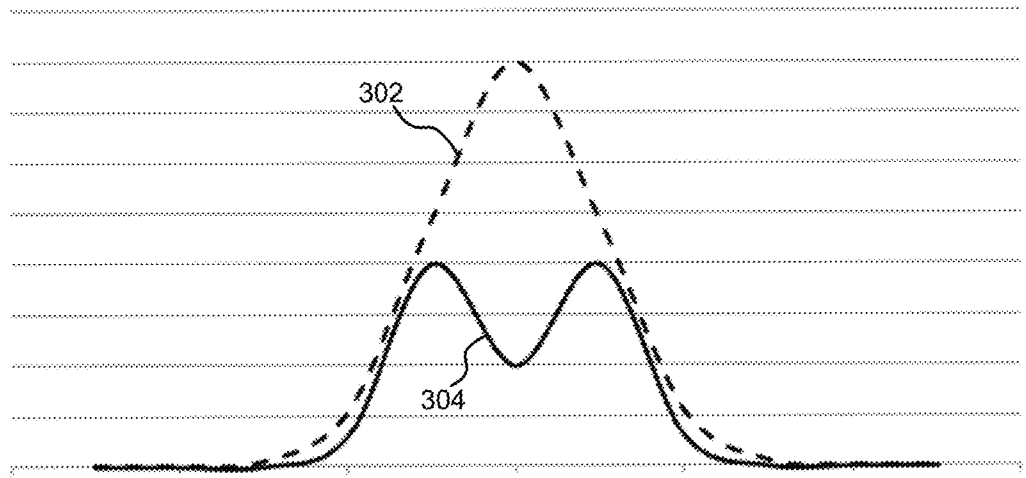
FIG. 3 is a cross-sectional view of images of two particles.

FIG. 3 shows example profiles of two different particles. Curve 302 corresponds to a Gaussian curve. By fitting the curve to a Gaussian fit, the particle whose image corresponds to curve 302 may be identified as a calibration particle. By contrast, curve 304 may correspond to a an assay particle (non-calibration particle). In this example, the detected fluorescence may come from material distributed on the surface of the particle. As such, the distribution of light will not be Gaussian and the particle can be identified as not being a calibration particle. These curves correspond to a cross section of the image shown in FIG. 2.

Figure 4:
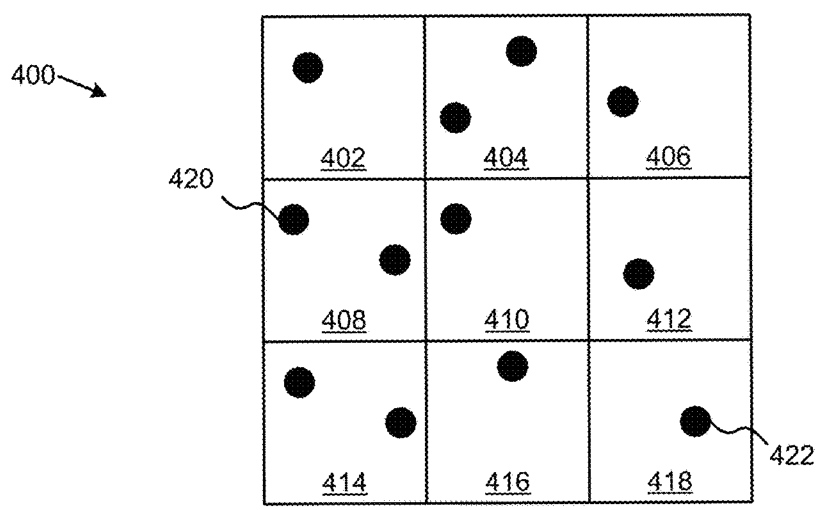
FIG. 4 is a representation of a two-dimensional image partitioned into nine regions for normalization.

FIG. 4 shows one example of how calibration particles 420 may be used to normalize an image. In this example, the image 400 is partitioned into nine regions (402, 404, 406, 408, 410, 412, 414, 416, and 418). Each region has one or more calibration particles 420. As described above, according to methods described herein, the calibration particles may be first identified as being calibration particles by the profile of their image. After the calibration particles are identified, the intensity of the calibration particles 420 may be measured as described above. That measured intensity may then be used to normalize measurements of non-calibration particles (not shown) in the image 400. Differences in image intensity, such as may be introduced by lighting non-uniformities, lens aberrations, or sensor imperfections, for example, may be compensated through this normalization. Although the example in FIG. 4 shows an image that is partitioned into nine regions, the partitions may be as few as one (the entire image is normalized uniformly, or may be unlimited. In the latter situation, a mathematical formula representing the normalization may be constructed. For reasons of explanation only, the mathematical formula representing the normalization may resemble a topographical map that shows how amount of normalization applies varies by location on the image.

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated and described in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation of Austin, Tex. The terms “particles” and “microspheres” are used interchangeably herein.

Some embodiments include a tangible computer-readable medium that includes computer-readable code that, when executed by a computer, causes a computer to perform at least one embodiment of the present methods. The tangible computer-readable medium may be, for example, a CD-ROM, a DVD-ROM, a flash drive, a hard drive or any other physical storage device.

In some methods, a tangible computer-readable medium is created. In some embodiments, the method may include recording the computer readable medium with computer readable code that, when executed by a computer, causes the computer to perform at least one embodiment of the present methods. Recording the computer readable medium may include, for example, burning data onto a CD-ROM or a DVD-ROM, or otherwise populating a physical storage device with the data.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. For example, the fits used to identify calibration particles are described as preferably being Gaussian fits. Other mathematical fits may be used that are within the spirit of the disclosed embodiments. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. A method comprising:

a computing system acquiring a two-dimensional image of a plurality of particles in a first channel, wherein the plurality of particles have been exposed to an analyte, wherein the plurality of particles includes a plurality of calibration particles having internal distributions of a first fluorescent material and a plurality of non-calibration particles having surface distributions of a second fluorescent material;

the computing system identifying a calibration particle of the plurality of calibration particles by analyzing first pixel values of first pixels that correspond to the calibration particle in the first channel to correlate intensity values of the first pixels to a Gaussian function;

the computing system identifying a non-calibration particle of the plurality of non-calibration particles by analyzing second pixel values of second pixels that correspond to the non-calibration particle in the first channel to determine that intensity values of the second pixels do not correlate to a Gaussian function;

the computing system measuring an intensity of the calibration particle based on the first pixel values; and the computing system saving a new version of the two-dimensional image, wherein the new version of the two-dimensional image includes third pixels with third pixel values that are normalized based at least in part on the intensity of the calibration particle.

2. The method of claim 1, wherein the acquiring includes capturing the two-dimensional image via an imaging detector.

3. The method of claim 2, wherein the imaging detector includes a charge coupled device (CCD) sensor.

4. The method of claim 1, wherein the plurality of calibration particles are distributed into a plurality of regions of the two-dimensional image, and wherein the third pixel values for pixels in a particular region are normalized based on intensities of the plurality of calibration particles in the particular region.

5. The method of claim 1, further comprising normalizing an intensity of a second two-dimensional image of the plurality of particles in a second channel based at least in part on the intensity of the calibration particle.

6. The method of claim 5, wherein the second channel is different from the first channel, and wherein the second channel is a classification channel.

7. The method of claim 1, wherein the new version of the two-dimensional image is usable to combine a plurality of images of the particles.

8. The method of claim 1, wherein the first fluorescent material is the same as the second fluorescent material.

9. A non-transitory, computer-readable medium having instructions stored thereon that, in response to execution by a computing system, cause the computing system to carry out operations comprising:

acquiring a two-dimensional image of a plurality of particles in a first channel, wherein the plurality of particles have been exposed to an analyte, wherein the plurality of particles includes a plurality of calibration particles having internal distributions of a first fluorescent material and a plurality of non-calibration particles having surface distributions of a second fluorescent material;

identifying a calibration particle of the plurality of calibration particles by analyzing pixel values of pixels that correspond to the calibration particle in the first channel to correlate brightness values of the pixels to a Gaussian function, wherein at least one non-calibration particle has brightness values in the first channel that do not correlate to a Gaussian function;

measuring a brightness of the calibration particle based on the pixel values; and saving a new version of the two-dimensional image, wherein the new version of the two-dimensional image includes new pixels with new pixel values that are normalized based at least in part on the brightness of the calibration particle.

10. The medium of claim 9, wherein the plurality of calibration particles include more than one first fluorescent material.

11. The medium of claim 9, wherein the first channel is a reporter channel, wherein the two-dimensional image is a reporter image, and wherein the new version of the two-dimensional image is usable to normalize pixel values in a classification image.

12. The medium of claim 9, wherein measuring the brightness of the calibration particle includes detecting a peak of the calibration particle.

13. The medium of claim 9, wherein measuring the brightness of the calibration particle includes integrating an area of the two-dimensional image around a center of the calibration particle.

14. The medium of claim 9, wherein the operations further comprise: determining a background brightness level for the two-dimensional image.

15. The medium of claim 14, wherein the operations further comprise: subtracting the background brightness level from the pixel values before identifying the calibration particle.

16. An apparatus, comprising:

at least one processor; and an imaging device including an imaging region;

wherein the imaging device is configured to operate in conjunction with a processor of the at least one processors to:

accept, into the imaging region, a plurality of particles that includes a plurality of calibration particles having internal distributions of a first fluorescent material and a plurality of non-calibration particles having non-internal distributions of a second fluorescent material;

supply light to the imaging region, wherein the light corresponds to a first channel; and capture an image of the plurality of particles in the first channel; and wherein the at least one processor is configured to:

identify a calibration particle of the plurality of calibration particles by analyzing first pixel values of first pixels that correspond to the calibration particle to correlate intensity values of the first pixels in the first channel to a Gaussian function;

identify a non-calibration particle of the plurality of non-calibration particles by analyzing second pixel values of second pixels that correspond to the non-calibration particle to determine that intensity values of the second pixels in the first channel do not correlate to a Gaussian function;

measure an intensity of the calibration particle; and normalize an intensity of the image based at least in part on the intensity of the calibration particle.

17. The apparatus of claim 16, wherein the identifying the calibration particle includes approximating the Gaussian function with a quadratic function.

18. The apparatus of claim 16, wherein the plurality of calibration particles are distributed into a plurality of regions of the image, and wherein the intensity of the image is normalized in a particular region based on intensities of the plurality of calibration particles in the particular region.

19. The apparatus of claim 18, wherein the at least one processor is further configured to partition the image into the plurality of regions based on a grid.

20. The apparatus of claim 18, wherein the plurality of regions is a continuous plurality of regions.

* * * * *